United States Patent [19]

Luria et al.

[11] Patent Number: 4,948,735
[45] Date of Patent: Aug. 14, 1990

[54] SYSTEM FOR RELEASE OF PROTEINS FROM MICROBE CELLS

[75] Inventors: Salvador E. Luria, Lexington; Joan L. Suit, Cambridge; Jennifer A. Jackson, Reading, all of Mass.

[73] Assignee: Repligen Corporation, Cambridge, Mass.

[21] Appl. No.: 11,579

[22] Filed: Feb. 6, 1987

[51] Int. Cl.$^5$ .......................... C12N 1/20; C12N 1/06; C12N 15/00; C12P 21/00

[52] U.S. Cl. ................................ 435/252.8; 435/69.1; 435/69.7; 435/69.8; 435/71.2; 435/252.33; 435/259; 435/320; 435/849; 935/47; 935/48

[58] Field of Search ........... 435/259, 320, 253, 252.33, 435/252.8, 849, 69.1, 69.7, 71.2, 69.8; 935/47, 48

[56] References Cited

FOREIGN PATENT DOCUMENTS 0216080 4/1987 European Pat. Off. .

OTHER PUBLICATIONS

Kudo et al., 1983, J. of Bacteriology 156: 949–951.
Pugsley et al., 1983, J of Bacteriology 156: 109–114.
Pugsley et al., 1984, Embo J. 3: 2393–2397.
Cole et al., 1985, MGG 198: 465–472.
Luirink et al., (Mar. 1986) J of Gen. Microbiology 132: 825–834.
Suit et al., 1988, J of Bacteriol. 170: 4963–4966.
Pugsley, A. P., and M. Schwartz (1984) "Colicin E2 Release: Lysis, Leakage or Secretion? Possible Role of a Phospholipase," The EMBO J. 3(10):2393–2397.
Suite, et al., (1985), J. Bacteriol. 161:944–948.
Sabik, J. F., Suit, J. L. and Luria, S. E. (1983) J. Bacteriol. 153:1479–1485.
Kobayashi, T. et al., (1986) J. Bacteriol. 166:728–732.
Altieri, M., Suit, J. L., Fan, M.-L. J. and Luria, S.E. (1986) J. Bacteriol. 168:648–654.

Primary Examiner—Charles E. Warren
Assistant Examiner—P. Rhodes
Attorney, Agent, or Firm—Saliwanchik & Saliwanchik

[57] ABSTRACT

The invention concerns novel and useful mutant microbes which are capable of releasing substantial amounts of any of several periplasmic or recombinant proteins into the culture medium when carrying an expressed Kil gene. Though *E. coli* are exemplified, the invention is broadly applicable to the making of mutants of other microbes, for example, *Salmonella*, *Klebsiella*, and *Rhizobium*. A key feature of the invention is the use of a novel selection procedure employing a plasmid comprising the kil gene.

7 Claims, 1 Drawing Sheet

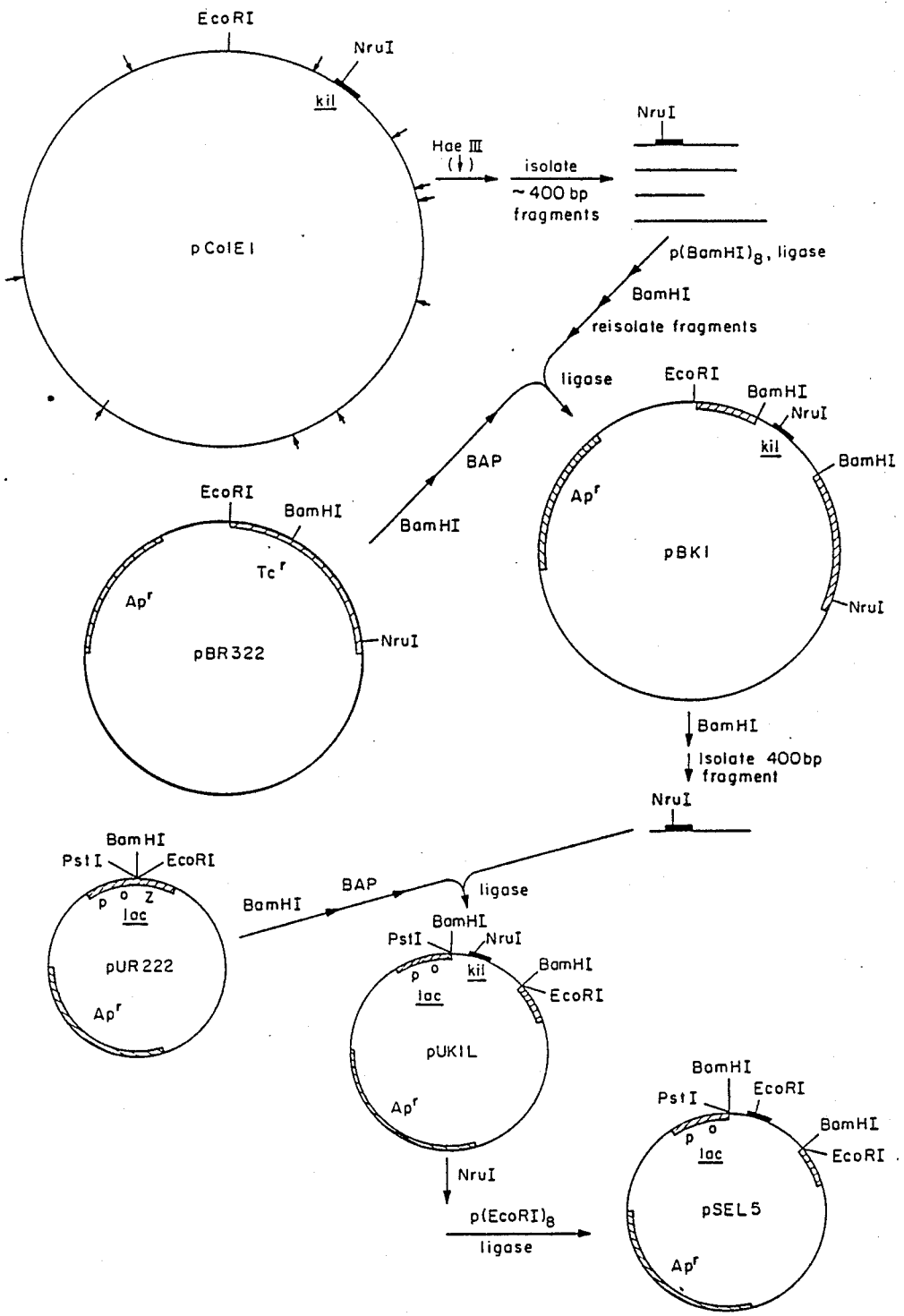

SYSTEM FOR RELEASE OF PROTEINS FROM MICROBE CELLS

Some of the work disclosed herein was supported by an NIH Support Grant number NIH-5-R01-AI03038.

BACKGROUND OF THE INVENTION

Many proteins of industrial and medical interest can effectively be produced by introducing the corresponding genes into microorganisms using genetic engineering techniques. A favorite microorganism for such production is *Escherichia coli*, whose genetic makeup is probably the best known of all organisms, and whose mutants lend themselves to elaborate manipulations.

Production of a protein in *E. coli* can yield very large amounts of protein, which must usually be purified to remove other proteins and bacterial components (including bacterial endotoxin).

It is desirable to devise a system such that the cells of *E. coli* will produce a desired protein and release it into the medium, thereby facilitating purification. With such a system, it may also be possible to collect secreted proteins in large amounts from *E. coli* cells growing under continuous flow conditions.

The kil gene is identified as an open frame in plasmid pColE1, the source of colicin El. The MIT group (Drs. S.E. Luria and J.L. Suit) have demonstrated the existence and the role of the kil gene: Expression of an intact kil gene located under the ColE1 promoter causes cell death and release of colicin El from the bacteria (Suit, et al. [1983]J. Bacteriol. 161:944–948). Colicin El, like all colicins, is produced in the cytoplasm, and is not located in the periplasm. Several other colicin-producing plasmids have been found to contain genes which function analogously to that of kil in pColE1 (Sabik, J.F., Suit, J.L. and Luria, S.E. [1983]J. Bacteriol. 153:1479–1485. The colicin-kil promoters in all these plasmids are inducible by treatment with mitomycin C. The protein product of kil has not yet been isolated; it is believed to be made as a peptide of 45 amino acids, which may be processed in vivo by proteolysis.

When the kil gene is expressed under a strong promoter, $kil^s$ cells of *E. coli* are rapidly killed. Recently Kobayashi et al. (Kobayashi, T. et al. [1986]J. Bacteriol. 166:728–732) reported that weak expression of kil (under an unknown weak promoter) causes release of two periplasmic proteins ($\beta$-lactamase and alkaline phosphatase) with little cell killing.

Recently, researchers at MIT published on the "Expression of the Cloned ColE1 kil Gene in Normal and $Kil^r$ *Escherichia coli*," (Altieri, M., Suit. J.L., Fan, M.-L.J. and Luria, S.E. [1986]J. Bacteriol. 168:648–654). This paper makes no mention of the ability of the prepared mutants to release periplasmic proteins into the medium. (Kobayashi et al., supra).

BRIEF SUMMARY OF THE INVENTION

Utilizing a novel selection process, novel and useful mutant microorganisms were made. These novel microorganisms are mutants of *E. coli* K12 A153 NRRL B-18164). These novel mutants are representative of two distinct classes possessing the common features of being resistant to the lysing action of the kil gene of ColE1 and pColE2, and, when carrying an expressed Kil gene, of being capable of releasing, advantageously, substantial amounts of any of several periplasmic *E. coli* or recombinant proteins into the culture medium. The specific mutants exemplified herein are prototypes of two classes of mutants which can be prepared by the novel process dislcosed herein. Mutants designated Class I release periplasmic proteins in amounts of about 20 to about 50% throughout the growth cycle, whereas mutants belonging to Class II release up to about 100% of periplasmic proteins only when they approach full growth in the culturing process.

BRIEF DESCRIPTION OF THE DRAWING

FIG. 1 Construction of plasmids pBLK1, pUK1L, and pSEL5. Abbreviations and symbols: (→) recognition site for HaeIII restriction endonuclease: p(BamHI)$_8$ and p(EcoRI)$_8$, 8-bp linkers containing the BamHI and EcoRI recognition sequences, respectively; ligase, T4 DNA ligase; BAP, bacterial alkaline phosphatase; kil, an opening reading frame of 138 bp on pColE1 containing a unique NruI recognition sequence; $Ap^r$ and $Tc^r$, genes coding for resistance to ampicillin and tetracycline, respectively; lac, the proximal part of the lactose operon including promoter (p) and operator (o) regions, plus a 30-bp insert containing the indicated restriction endonuclease recognition sequences and the first few base pairs of the gene coding for B-galactosidase(Z).

DETAILED DESCRIPTION OF THE INVENTION

The following deposits of cultures disclosed in this application have been made in the Agricultural Research Culture Collection (NRRL), Northern Regional Research Center, U.S. Department of Agriculture, 1815 North University Street, Peoria, Ill. 61604, USA

| Culture | Repository No. | Deposit Date |
| --- | --- | --- |
| *E. coli* K12 A153 | NRRL B-18164 | Jan. 30, 1987 |
| *E. coli* K12 A153 $kil^R$I-1(pUK1L) | NRRL B-18165 | Jan. 30, 1987 |
| *E. coli* K12 A153 $kil^R$II-1(pUK1L) | NRRL B-18166 | Jan. 30, 1987 |
| *E. coli* K12 A153 $kil^R$I-1(pUK1L) (pAOmpA) | NRRL B-18167 | Jan. 30, 1987 |

The subject cultures have been deposited under conditions that assure that access to the cultures will be available during the pendency of this patent application to one determined by the Commissioner of Patents and Trademarks to be entitled thereto under.37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits.

All restrictions on the availability to the public of the subject culture deposits will be irrevocably removed upon the granting of a patent disclosing them.

REFERENCE TO THE TABLES

Table 1—Release of Enzymes from *Escherichia coli* A153 I-1 carrying pUK1L

Table 2—Release of β-Lactamase from Kil$^r$ Mutants Carrying pUK1L

Table 3—Release of Enzymes from *Escherichia coli* W31101q (pUK1L )

Table 4—Qualitative Estimate of Hybrid Protein A Released

UTILITY

The expression system described herein using healthy Kil$^r$ mutants and the kil gene to release periplasmic proteins into the culture medium is of great utility in producing proteins of medical and industrial importance. The advantage of this system is that the desired protein should be easier to purify from other bacterial proteins and bacterial endotoxins. In addition, the desired protein can be produced under continuous culture conditions. Proteins of mammalian or plant origin engineered to be periplasmic in bacteria will also be released. Examples of mammalian proteins that have been placed in the bacterial periplasm include human epidermal growth factor (Oka, T. et al. [1985]Proc. Natl. Acad. Sci. 82:7212–7217) and human interferon alpha 2 (Barbero, J.L. et al. [1986]J. of Biotechnology 4: 255–267). Some important plant proteins, including ribulose diphosphate carboxylase and leguminous hemoglolin, have also been cloned into *E. coli*. The release of these periplasmic proteins into the culture medium will be of great utility. Examples of other proteins that can be produced using the invention system include, but are not limited to, medically important proteins such as IL-1 and HTLV-III proteins, and industrial enzymes such as ligninases and glucanases.

Scope of Bacterial Hosts

Bacterial hosts other than *E. coli* can be used in the subject invention by transferring the kil gene, either in pUK1L or pColE1 plasmid, to Kil$^r$ mutants such as Salmonella or Klebsiella. Further, the kil gene can be transferred to Rhizobium by mating. The procedures for transferring the kil gene are well known to persons skilled in the art.

The kil gene also can be transferred by making cointegrates of pUK1L with plasmids such as R300B (incompatibility iQ group) that can enter by mating into Pseudomonas and other organisms.(See Barth, Tobin, and Sharpe, Development of broad host-range plasmid vectors, in Molecular Biology, Pathogenicity, and Ecology of Bacterial Plasmids, S.B. Levy, R.C. Clowes, and E.L. Koenig, eds. New York, Plenum, 1981, pp.439–443.)

Construction of plasmids pBK1, pUK1L, and pSEL5

The construction of plasmids pBK1, pUK1L, and pSEL5 is outlined in FIG. 1. The probable site of the kil gene of pColE1 is downstream from the cea gene, very near the imm gene (Sabik, J.F., J.L. Suit, S.E. Luria [1983] "cea-kil operon of the ColE1 plasmid," J. Bacteriol. 153:1479–1485; Zhang, S., A. Faro, G. Zubay [1985] "Mitomycin-induced lethality in *Escherichia coli* cells continuing the ColE1 plasmid: involvement of the kil gene," J. Bacteriol. 163:174–179). In this region there is an open reading frame of 138 bp, lying in a 412-bp DNA fragment bracketed by two HaeIII sites and containing the only NruI site on the ColE1 plasmid (Chan, P.T., H. Ohmori, J. Tomazawa, J. Lebowitz [1985] "Nucleotide sequence organization of ColE1 DNA," J. Biol. Chem. 260:8925–8935; Dougan, G., M. Saul, G. Warren, D. Sherrat [1978] "A functional map of plasmid ColE1," Mol. Gen. Genet. 148:325–327; Oka, A., N. Nomura, M. Morita, H. Sugisaki, K. Sugimoto, M. Takanami [1979] "Nucleotide sequence of small ColE1 derivatives: structure of the regions essential for autonomous replication and colicin E1 immunity," Mol. Gen. Genet. 172:151–159). DNA fragments approximately 400 bp long produced by HaeIII digestion of pColE1 were cloned into the unique BamHl site of pBR322. The desired product was identified as a plasmid conferring resistance to ampicillin but not tetracycline and containing two NruI sites and was called pBK1. The inserted fragment presumed to contain the kil gene was isolated from a BamHl digest of pBK1 and cloned into the unique BamHl site of the plasmid pUR222, which contains the lac promoter and the first part of the IacZ gene as well as an Ap$^r$ marker. Recombinant plasmids with DNA inserted into the cloning site gave rise to Ap$^r$ transformants of *E. coli* RRIΔM15 that were white on LB azar plates containing 5-bromo-4-chloro-3-indolyl-β-D -galactopyranoside an indicator (Ruther, U., M. Koenen, K. Otto, B. Muller-Hill [1981] "pUR22 a vector for cloning and rapid chemical sequencing of DNA," Nucleic Acids Res. 9:4087–4098). Plasmids were isolated from such transformed cells, and those that released a 300 bp fragment upon double digestion with NruI and EcoR1 were considered to be pUR222 derivatives in which the kil gene DNA fragment has been inserted in the direction of transcription of the lac promoter. One such plasmid was then called pUK1L.

Plasmid pSEL5 was constructed by inserting a synthetic EcoR1 linker into the NruI site in the kil gene and was identified as an Ap$^r$ plasmid that was nonlethal to strain A153. Restriction enzyme tests showed it to have two EcoR1 sites 300 bp apart and no NruI site.

Following are examples which illustrate procedures for practicing the invention. These examples should not be construed as limiting. All percentages are by weight and all solvent mixture proportions are by volume unless otherwise noted.

EXAMPLE 1

Selection of bacterial cells

*E. coli* K12 A153 cells were subjected to genetic manipulations as follows: Cells of A153 were transformed with plasmid DNA, that of either pDMS630 (available from Dartmouth Medical School) and having the following relevant features: pColE1::Tn3(Ap$^r$, a that is, a kil gene together with a gene for ampicillin resistance or cea$^-$ deletion derivatives of it, and 22 individual Ap$^r$ transformants were subjected to several successive cycles of treatment with mitomycin C. For each cycle of treatment, an overnight culture was diluted 1/50 and incubated at 37° C with shaking for about 3 h and then with mitomycin C (2 μg/ml) for 2 h, at which time survival was 0.01 to 0.1%. The culture was then diluted 10$^{-5}$ and incubated overnight. After 3 to 5 such cycles, cultures were streaked out for isolated colonies on LB-ampicillin plates. (LB medium: 10 g/l bacto-tryptone, 5 g/l bacto-yeast extract, 10 g/l NaCl, pH 7.5). Five colonies were picked from each plate, grown up, treated for 2 h with mitomycin C, and tested by scoring for the time of appearance of visible growth. Cultures that showed greater survival than the parent control were retained and rechecked by measuring culture turbidity at intervals after the addition of mitomycin C. Those that did not show the loss of turbidity typical for mitomycin C-induced cells with kil+ plasmids were the putative Kil-resistant (Kil$^r$) mutants. Each putative Kil$^r$ isolate was put through the usual plasmid DNA amplification and extraction procedures. When plasmid DNA was found, it was used to transform A153 cells to Ap$^r$, and the transformants were checked for normal kil+ expression upon mitomycin C induction. Of 37 putative resistant mutants tested in this way, 34 were found to contain a kil+ plasmid.

Other compounds which can be used in the selection medium in place of ampicillin are those for which a resistance gene is found on the plasmid containing the kil gene. For example, the plasmid can contain a tetracycline resistance gene, which would then require the presence of tetracycline in the selection medium.

Twelve mutants were screened for sensitivity or resistance to the following agents thought likely to detect changed membrane properties: methylene blue, acriflavine, EDTA, neomycin, and deoxycholate. The screen used LB plates into which the chemicals had been incorporated at various concentrations, and the plates were scored for growth after incubation at 30° C. The mutants fell into three classes: class I (one mutant), sensitive to EDTA, neomycin, and deoxycholate (no growth at concentrations of 2 mM, 1 $\mu$g/ml, and 1%, respectively): class II (eight mutants) resembling the control strain (growth at concentrations of 5 mM, 2 $\mu$g/ml, and 3%, respectively): and class III (three mutants) resistant to 6 $\mu$g of neomycin per ml. The response to methylene blue or to acriflavine was normal in all isolates.

One representative of each of these classes was cured of its resident plasmid. The cured strains were designated I-1, II-1, and III-1, respectively, and were studied further. Each was found to display the same response to EDTA, neomycin, and deoxycholate as before being cured. The growth of mutant II-1 was found to be slow at temperatures above 35° C, so all incubations were carried out at that or lower temperatures. Mutant III-1 grew somewhat more slowly than the parent and the other mutants at all temperatures.

The above procedure is disclosed in Altieri et al., supra. This publication is incorporated herein by reference thereto.

Mutants Kil$^r$ I-1 and II-1 are prototypes of two classes of mutants isolated in the above way. Many such mutants, Kil$^r$ I and Kil$^r$ II, can be obtained by the above procedure.

The Kil$^r$ I-1 and II-1 strains were cured of the pColE1 plasmid and individual cultures of cured cells were transformed with plasmid pUK1L, constructed as shown in Altieri, suora, in which the kil gene from pColE1 is placed under the promoter-operator of the lac operon. The cells have no lac repressor; hence the kil gene is maximally expressed. Both Kil$^r$ I-1 and Kil$^r$ II-1 cells were fully resistant to kil expression.

The cells of Kil$^r$ I-1 (pUK1L) released 20 to 50% of their periplasmic enzymes B-lactamase and alkaline phosphatase throughout their growth. Cells of Kil$^r$ II-1 (pUK1L) only release periplasmic enzymes (50-100%) in aging cultures.

The role of mutations I and II in release of protein is specific. A third class of mutants, Kil$^r$ III, does not release any significant amounts of periplasmic proteins.

EXAMPLE 2

Release of recombinant protein A from the periplasm

The protein A gene from *Staphylococcus aureus* was cloned behind the *E. coli* ompA signal sequence. First, EcoRI linkers were ligated to a 1.1 kb Fnu4HI fragment containing the protein coding sequence of protein A. Second, the fragment with EcoRI ends was ligated into the EcoRI site of the secretion cloning vector pIN-III-ompA (Ghrayeb, J. et al. [1984]EMBO Journal 3:2437-2442). Finally, this plasmid was made chloramphenicol-resistant and ampicillin-sensitive by inserting the CAT (chloramphenicol acyltransferase) gene into the bla ($\beta$-lactamase) gene. The resultant plasmid, pAompA, conferred chloramphenicol resistance and directed the production and location of protein A into the periplasmic space. Protein A can be recovered from the periplasmic space by the same well-known procedures by which one can selectively extract $\beta$-lactamase and alkaline phosphatase (but none of the cytoplasmic enzymes). In the absence of a Kil gene, cells with plasmid pAOmpA do not release any of the periplasmic proteins into the medium.

Tables 1-4 illustrate typical findings of enzyme secretion of periplasmic enzymes, as well as the failure of secretion when the kil gene is inactive. They also show that cells secreting periplasmic enzymes do not secrete significant amounts of a cytoplasmic enzyme, $\beta$-galactosidase, indicating that protein release is not a simple consequence of cell lysis.

TABLE 1

Release of Enzymes from *Escherichia coli* A153 I-1 Carrying pUK1L

| | | $\beta$-lactamase | | | $\beta$-D-galactosidase | | |
|---|---|---|---|---|---|---|---|
| A. Plasmid | Sample | Total | Free | % Free | Total | Free | % Free |
| pUK1L | 1 | — | 32 | — | 1.23 | 0.007 | 0.6 |
| | 2 | 200 | 128 | ~50 | 3.38 | 0.235 | 1.1 |
| | 3 | 800 | 512 | 60 | 37.6 | 0.1 | 0.3 |
| pSEL5 | 1 | 100 | 4 | 4 | 1.17 | 0.008 | 0.48 |
| | 2 | 200 | 16 | 8 | 9.8 | 0.007 | 0.08 |
| | 3 | 800 | 16 | 2 | 45.0 | 0.008 | 0.02 |

| | alkaline phosphatase | | |
|---|---|---|---|
| B. | Total | Free | % Free |
| pUK1L | 0.032 | 0.007 | 21.00 |
| PSEL5 | 0.048 | 0.001 | 0.02 |

TABLE 2
Release of β-lactamase from Kil' Mutants Carrying pUK1L

| Mutant | Plasmid | β-Lactamase Total | Free | % Free |
|---|---|---|---|---|
| II-1 | pUK1L | 128 | 128 | 100 |
|  | pSEL5 | 256 | 8 | 3 |
| III-1 | pUK1L | 64 | 4 | 6 |
|  | pSEL5 | 64 | 4 | 6 |

Methods are as given in Table 1. The bacteria were taken from overnight cultures. β-lactamase titers are in empirical units from 1:2 serial dilutions.

TABLE 3
Release of Enzymes from *Escherichia coli* W31101$^q$ (pUK1L)

| Plasmid | Sample | β-lactamase Total | Free | % Free | β-D-galactosidase Total | Free | % Free |
|---|---|---|---|---|---|---|---|
| pUK1L | a | 400 | 200 | 50 | 43 | 2.1 | 5.0 |
|  | b | 1600 | 1600 | 100 | 217 | 7.8 | 3.4 |
| pSEL5 | a | 400 | 40 | 10 | 113 | 2.6 | 2.3 |
|  | b | 1600 | 80 | 5 | 240 | 2.4 | 1.0 |

Cultures of W31101$^q$ carrying either pUK1L or pSEL5 were grown first with isopropyl-β-D-thiogalactopyranoside (IPTG, Sigma Chemical, St. Louis, MO) (0.02 mM) to induce expression of the kil gene and of β-D-galactosidase (samples a), then for 2 h without IPTG (samples b). Assay was done as in Table 1.

TABLE 4
Qualitative Estimate of Hybrid Protein A Released

| Strain | A153 I-1 (pAOmpA) Cells | Medium | Wash | A153 I-1 (pAOmpA, pUK1L) Cells | Medium | Wash |
|---|---|---|---|---|---|---|
| Relative Amount Hybrid Protein A | 99% | 1% | — | 80% | 7% | 13% |

Cells of *Escherichia coli* A153 I-1 (pAOmpA) with or without pUK1L were grown at 30° C in LB broth overnight. Maintenance of both plasmids required a double drug selection. A153 I-1 (pAOmpA) was grown in LB broth with 10 μg/ml chloramphenicol; A153 I-1 (pAOmpA: pUK1L) with 10 μg/ml chloramphenicol and 50 μg/ml ampicillin. Culture samples were centrifuged to remove medium from cells and the cells were washed once with 10 mM Tris pH 8.0, 1 mM EDTA for 10 min and recentrifuged to separate cells from wash. Fractionated culture samples were assayed for relative amounts of hybrid protein A by Western analysis (Maniatis, T., Fritsch, E.F. and Sambrook, J., *Molecular Cloning: A Laboratory Manual*, Cold Spring Harbor Laboratory, Cold Spring Harbor, NY [1982]) Protein A was visualized by reaction with rabbit IgG conjugated to horseradish peroxidase (Sigma). 4-chloro-1-naphthol was used as the substrate. Serial dilutions of fractionated culture samples allowed a relative estimation of the amount of hybrid protein A in each fraction.

We claim:

1. *E. coli* mutant microbes, designated Class I, characterized as follows:
    (a) fully resistant to the lysing action of the kil gene of pColE1 or other such gene with kil-type activity;
    (b) capable of releasing substantial amounts of any of several periplasmic *E. coli* or recombinant proteins into the culture medium when carrying an expressed kil gene or other gene with kil-type activity;

and being further characterized as
    (c) capable of releasing periplasmic proteins in amount of about 20 to about 50% throughout the growth cycle.

2. *E. coli* mutant microbes, designated Class II, characterized as follows:
    (a) fully resistant to the lysing action of the kil gene of PColE1 or other such gene with kil-type activity;
    (b) capable of releasing substantial amounts of any of several periplasmic *E. coli* or recombinant proteins into the culture medium when carrying an expressed kil gene or other gene with kil-type activity;

and being further characterized as
    (c) capable of releasing periplasmic proteins in amounts of about 50 to about 100% only when they approach full growth in the culturing process.

3. *E. coli* K12 A153 kil®I-1(pUKIL), a microbe according to claim 1.

4. *E. coli* K12 A153 kil²®II-1(pUKIL), a microbe according to claim 2.

5. *E. coli* K12 A153 kil®I-1(pUKIL)(pAOmpA), a microbe according to claim 1.

6. The *E. coli*, according to claim 1, wherein said other gene with kil-type activity is the kil-type gene of pColE2.

7. The *E. coli*, according to claim 2, wherein said other gene with kil-type activity is the kil-type gene of pColE2.

* * * * *

UNITED STATES PATENT AND TRADEMARK OFFICE
CERTIFICATE OF CORRECTION

PATENT NO. : 4,948,735

DATED : Aug. 14, 1990

INVENTOR(S) : Luria et al.

It is certified that error appears in the above-identified patent and that said Letters Patent is hereby corrected as shown below:

| | |
|---|---|
| Column 2: | Line 48: ".37" should read --37--. |
| Column 3: | Line 33: "hemaglolin" should read --hemaglobin--. |
| Column 4: | Line 22: "IacZ" should read --lacZ--. |
| Column 4: | Line 26: "azar" should read --agar--. |
| Column 4: | Line 55: "($A_p{}^r$, a" should read --($A_p{}^r$),-- |
| Column 6: | Line 6: "suora" should read --supra--. |
| Column 6: | Table 1: Please add the following paragraph |

--Cells of E. coli A153 I-1 (pUK1L) or I-1 (pSEL5) were grown at 30°C in LB broth with 20 ug/ml ampicillin (to eliminate any plasmid-less derivatives). At one or more times, samples were taken. One fraction was centrifuged and the supernatant was used to assay free enzyme. Another fraction was extracted in $CH^3Cl$ alone or with SDS and used for assay of total enzyme.

Alkaline phosphatase and ß-D-galactosidase assays were performed by standard methods. ß-galactosidase was assayed by using 1:2 serial dilutions of each sample with a fixed amount of a fresh ampicillin solution . After 30 min. incubation at 35°C, each sample was spotted on a lawn of ampicillin-sensitive bacteria. The titers (inverse of the highest dilution that still inhibited growth) are accurate within a factor of 2.--

UNITED STATES PATENT AND TRADEMARK OFFICE
CERTIFICATE OF CORRECTION

PATENT NO.  : 4,948,735          PAGE 2 OF 2

DATED       : Aug. 14, 1990

INVENTOR(S) : Luria et al.

It is certified that error appears in the above-identified patent and that said Letters Patent is hereby corrected as shown below:

Column 8: E.coli K12 A153    Line 38: "E.coli K12 A153 kil®I-1(pUKIL)," should read -- kil$^R$I-1(pUK1L),--.

Column 8: E.coli K12    Line 40: "E.coli K12 A153 kil$^{2®}$II-1(pUKIL)," should read -- A153 kil$^R$II-1(pUK1L)--.

Column 8: E.coli K12 A153    Line 42: "E.coli K12 A153 kil®I-1(pUKIL)" should read -- kil$^R$I-1(pUK1L)--.

Signed and Sealed this

Fourth Day of February, 1992

Attest:

HARRY F. MANBECK, JR.

*Attesting Officer*    Commissioner of Patents and Trademarks